United States Patent [19]

Aoki et al.

[11] Patent Number: 4,662,755
[45] Date of Patent: May 5, 1987

[54] GAS ANALYZER WITH MEANS FOR VARYING ANGLE OF INCIDENCE OF LIGHT ON INTERFERENCE FILTER

[75] Inventors: Junji Aoki; Kennosuke Kojima, both of Miyanohigashi, Japan

[73] Assignee: Horiba, Ltd., Kyoto, Japan

[21] Appl. No.: 721,633

[22] Filed: Apr. 9, 1985

[30] Foreign Application Priority Data

Apr. 10, 1984 [JP] Japan .................................. 59-72273

[51] Int. Cl.⁴ ............................................. G01N 21/00
[52] U.S. Cl. .................................... 356/414; 250/343
[58] Field of Search ............... 250/343, 345, 347, 373; 356/414, 416

[56] References Cited

U.S. PATENT DOCUMENTS 3,940,623 2/1976 Hempowitz et al. ............... 250/343

Primary Examiner—Eugene R. LaRoche
Assistant Examiner—James C. Lee
Attorney, Agent, or Firm—Wenderoth, Lind & Ponack

[57] ABSTRACT

A gas analyzer provided with apertures on the optical paths from a light source through a cell to sensors and multi-layer interference band-pass filters on the respective optical paths. The structure makes it possible to change the distance between each sensor and the corresponding aperture, or the change the size of the aperture, for changing the maximum angle of incidence of light on the filters which is sensed by the sensors to thus change the central wavelength of the filters.

4 Claims, 10 Drawing Figures

GAS ANALYZER WITH MEANS FOR VARYING ANGLE OF INCIDENCE OF LIGHT ON INTERFERENCE FILTER

BACKGROUND OF THE INVENTION

1. Field of the Invention

This invention relates to a gas analyzer provided with a multilayer interference filter on an optical path extending from a light source through a cell to a detector.

2. Description of the Prior Art

The multilayer interference filter used in a gas analyzer is usually a band-pass filter. It is important for such a bandpass filter to have a specific wavelength as a central wavelength because the specific central wavelength is the wavelength corresponding to the analyzer in which the filter is installed. Such band-pass filters are generally produced by vacuum depositing about 100 layers of a thin film which is about 0.05 $\mu$m thick on a filter substrate. The accuracy of the film thickness is required to be 0.5% or less in order to obtain the required specific central wavelength.

From the standpoint of manufacturing technique for such a multilayer film interference filter, it is difficult to manufacture the filters with a specific central wavelength, and in practice the specific wavelengths can be determined only after manufacturing. Hence, the number of usable multilayer interference filters is very limited. Only a slight difference of the central wavelength from the desired wavelength requires discarding the filter. The manufacturing process thus has a low yield of filters. The multilayer interference filters are usually expensive, the low yield resulting in a high manufacture cost for each usable filters.

OBJECT AND BRIEF SUMMARY OF THE INVENTION

The present invention has been developed based on the property of the multilayer interference filter that when an angle of incidence of the light filtering thereon changes, the central wavelength shifts.

An object of the invention is to provide a gas analyzer, which is usable even when the central wavelength of the interference filter differs from the specific wavelength required for the analyzer, by shifting the central wavelength of the filter to the desired specific wavelength.

In order to attain the above object, the gas analyzer of the invention is provided with at least one aperture along an optical axis from a light source through the cell to at least one detector and at least one multilayer interference filter positioned so that the distance between the detector and the aperture in the direction of the optical axis is variable.

This invention makes possible the adjustment of the maximum angle of incidence of the light from the cell on the filter, whereby any discrepancy in the central wavelength from the desired wavelength can be eliminated. This makes possible the use of filters which have central wavelengths which vary more widely from the desired central wavelengths, whereby the yield of multilayer film interference filters from the above described manufacturing method is remarkably improved, and the manufacturing cost for the usable filters is reduced.

Since the central wavelength of the multilayer interference filters can be shifted, it makes it possible, for example, to improve the relative sensitivity between propane and n-hexane, the $CO_2$ calibration curve, and interference influence on the HC measurement. The present invention is also usable to make possible an intentional fine shift of the central wavelength of the filter.

This and other objects of the invention will become more apparent from the detailed description and examples which follow.

DESCRIPTION OF THE PREFERRED EMBODIMENT

Figure 1:
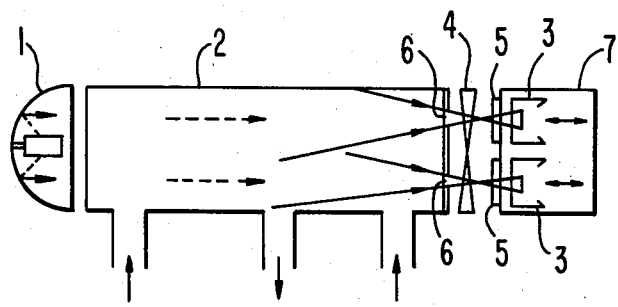
FIG. 1 is a schematic sectional view of an embodiment of a gas analyzer according to the invention.
Figure 2:
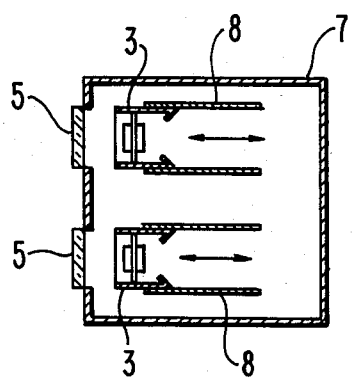
FIG. 2 is a sectional view of the sensor of the gas analyzer of FIG. 1 showing how the sensors move.
Figure 2A:
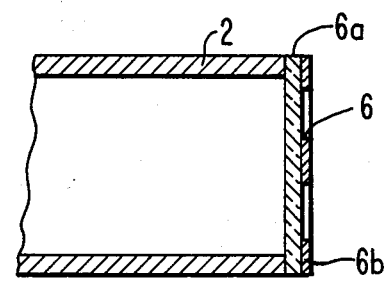
FIGS. 2a–2c are partial sectional views of embodiments of the aperture defining means.
Figure 2B:
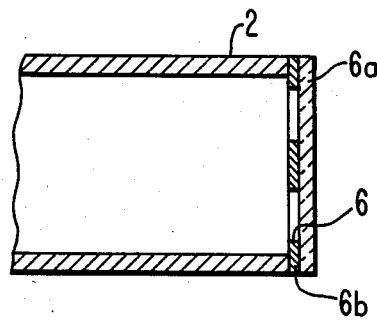
Figure 2C:
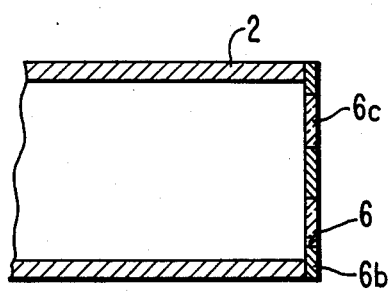
Figure 3A:
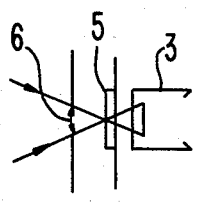
FIGS. 3a and 3b show variations in the maximum angle of incidence of light on the multilayer interference filter when the sensors are in different positions.
Figure 3B:
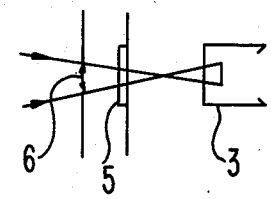

Referring to FIG. 1, the analyzer has a light source 1 at one end of a cell 2, and optical sensors 3, for example, pyroelectric sensors, at the other end. A chopper 4 is provided along the optical path from the light source 1 to the sensors 3. Multilayer interference filters 5 are mounted on sensor housing 7, and aperture defining means defining apertures 6 are provided in the end wall of cell 2 at the end opposite the light source 1, the corresponding aperture 6, multilayer interference filters 5 and sensors 3 being on the respective optical paths. The aperture defining means can have several forms. A window 6a of light permeable material such as calcium fluoride can cover the entire end of the cell 2 and have a plate 6b of light impermeable material with the apertures therein over the outside thereof as shown in FIG. 2a, or the window and plate can be reversed, as shown in FIG. 2b. Alternatively the apertures 6 in plate 6b can be filled with light permeable material 6c, as shown in FIG. 2c. The sensors 3 are slidably mounted in guide cylinders 8 in sensor housing 7 which have the cylindrical axes thereof lying along the optical paths as shown in FIG. 2. Such construction allows the light from the light source 1 to be reflected by the mirrored inner source of the cell 2 and diaphragmed by the aperture 6 so as to be incident on the light receiving surface of each sensor 3 with the maximum angle as shown in FIG. 1. In this case, when the sensors 3 are moved along the optical path, distances between the sensors 3 and the apertures vary so that the maximum angle of light falling on the respective multilayer interference filters 5 and then sensed by the sensors varys. The maximum angle of incidence of the sensed light on the multilayer interference filter 5, when each sensor 3 is moved toward the aperture 6, becomes larger as shown in FIG. 3a, and when the sensor 3 is moved away from the aperture 6, the angle of incidence becomes smaller as shown in FIG. 3b.

Figure 4:
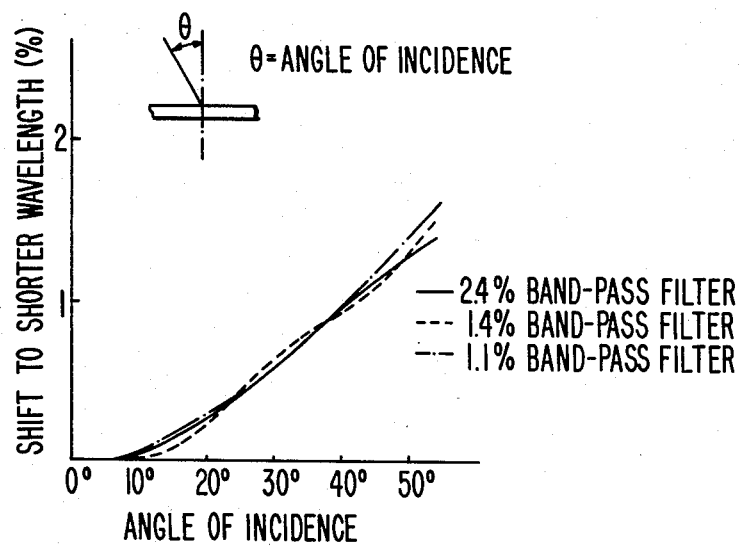
FIG. 4 is a graph for explaining the relation between the central wavelength and the maximum angle of incidence of light on a multilayer interference filter.

The central wavelength of the multilayer interference filter, changes as the angle of incidence changes, as shown in FIG. 4, so that even if the central wavelength of a multilayer interference filter incorporated into an analyzer differs from the central wavelength which is necessary for the anlayzer, the sensors 3 are moved in a direction to eliminate the difference. Hence, a multilayer interference filter having a central wavelength which differs from that required for the analyzer becomes usable, thereby remarkably improving the yield of multilayer interference filter production method.

Figure 5:
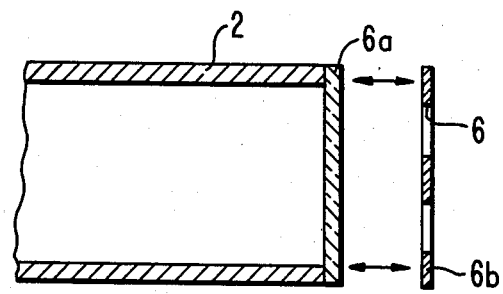
FIG. 5 shows an alternative embodiment in which the apertures are movable.
Figure 6:
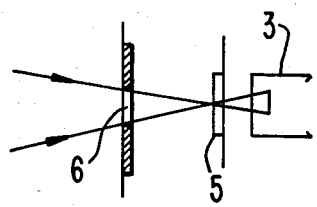
FIG. 6 shows a further alternative embodiment in which the diameter of the aperture is changeable.

In the aforesaid embodiment the sensors 3 are movable. Alternatively they may be fixed and the aperture defining means may be movable as shown in FIG. 5. in which the plate of FIG. 2a is moved toward sensors 3. Such a construction also can vary the angle of the incidence on the multilayer interference filter. Alternatively, the diameter of the aperture can be made changeable so that the angle of incidence of sensed light on the multilayer interference filter can be changed as shown in FIG. 6, for example by an iris diaphragm, thereby improving the yield of the filter production method. Furthermore, the chopper 4, which is shown as being between the cell 2 and the sensor 3, may of course be provided between the light source 1 and the cell 2.

While embodiments of the invention have been shown and described, the invention is not limited to the specific constructions thereof, which are merely exemplary in the specification.

What is claimed is:

1. A gas analyzer comprising:
   a cell;
   a light source at one end of said cell;
   at least one aperture defining means at the other end of the cell defining at least one aperture lying along an optional axis through the cell for directing a beam of light out of the cell;
   an optical sensor outside the other end of the cell along the optical axis for receiving light from said aperture;
   a multilayer interference band-pass filter positioned between said aperture and said sensor, the space between said aperture defining means and said optical sensor being free of any means for breaking up the shape of the beam of light from said aperture defining means;
   the entirety of aperture defining means, the entirety of said filter and the entirety of said sensor being relatively movable along the optical axis for varying the distance between said sensor and said aperture.

2. A gas analyzer as claimed in claim 1 in which only said sensor is movable along said optical axis.

3. A gas analyzer as claimed in claim 1 in which only said aperture defining means is movable along said optical axis.

4. A gas analyzer comprising:
   a cell;
   a light source at one end of said cell;
   at least one aperture defining means at the other end of the cell defining at least one aperture lying along an optical axis through the cell for directing a beam of light out of the cell;
   an optical sensor outside of the other end of the cell along the optical axis for receiving light from said aperture;
   a multilayer interference band-pass filter positioned between said aperture and said sensor, the space between said aperture defining means and said optical sensor being free of any means for breaking up the shape of the beam of light from said aperture defining means; and
   means forming part of said aperture defining means for varying the size of said aperture around the entire periphery thereof.

* * * * *